(12) United States Patent
Eastman et al.

(10) Patent No.: US 9,597,229 B2
(45) Date of Patent: Mar. 21, 2017

(54) PHACOEMULSIFICATION FLOW RATE DETECTION SYSTEM AND METHOD

(71) Applicant: Abbott Medical Optics Inc., Santa Ana, CA (US)

(72) Inventors: Brian J Eastman, Irvine, CA (US); Kelvin Kao, Long Beach, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 148 days.

(21) Appl. No.: 13/836,011

(22) Filed: Mar. 15, 2013

(65) Prior Publication Data

US 2014/0276372 A1    Sep. 18, 2014

(51) Int. Cl.
*A61F 9/007* (2006.01)
*A61M 3/02* (2006.01)
*G01F 1/06* (2006.01)

(52) U.S. Cl.
CPC ...... *A61F 9/00745* (2013.01); *A61F 9/00736* (2013.01); *A61M 3/0283* (2013.01); *G01F 1/065* (2013.01)

(58) Field of Classification Search
CPC .......... A61F 9/00781; A61F 2250/0068; A61F 9/007; A61F 9/0017; G01F 1/661; G01F 1/7086; G01F 1/662; G01F 1/00; G01F 1/10; G01F 1/05; G01F 1/103; G01F 23/2922; A61M 1/0031; G01P 3/486; G01P 5/06; G01D 5/30
USPC .......................................... 604/294, 290, 52
See application file for complete search history.

(56) References Cited

U.S. PATENT DOCUMENTS

| | | | | |
|---|---|---|---|---|
| 2,723,562 A * | 11/1955 | Lutz et al. | ................. | 73/861.77 |
| 3,043,143 A * | 7/1962 | Hollmann | ................. | 73/861.91 |
| 3,217,539 A * | 11/1965 | Owen et al. | ............... | 73/861.77 |
| 3,364,359 A * | 1/1968 | Cronin | ..................... | 250/231.16 |
| 3,563,090 A * | 2/1971 | Deltour | .............. | A61M 5/1689 |
| | | | | 128/DIG. 13 |
| 3,570,311 A * | 3/1971 | Nelson | .......................... | 73/327 |
| 3,788,285 A * | 1/1974 | Gelin | ..................... | F02D 41/00 |
| | | | | 123/484 |
| 3,879,136 A * | 4/1975 | Takeda | ......................... | 356/447 |
| 3,915,570 A * | 10/1975 | Skala | ............................. | 356/73 |
| 3,983,391 A * | 9/1976 | Clemons | .................. | 250/237 G |
| 4,324,144 A * | 4/1982 | Miyata et al. | ............ | 73/861.77 |
| 4,348,906 A * | 9/1982 | Feller | ........................ | 73/861.77 |
| 4,428,243 A * | 1/1984 | Taylor | ....................... | 73/861.77 |
| 4,500,870 A * | 2/1985 | Krohn et al. | .................. | 341/14 |
| 4,566,317 A * | 1/1986 | Shakra | ....................... | 73/152.35 |
| 4,606,223 A * | 8/1986 | Matsunaga et al. | ....... | 73/114.25 |
| 4,612,806 A * | 9/1986 | Feller | ............................. | 73/195 |

(Continued)

FOREIGN PATENT DOCUMENTS

| | | |
|---|---|---|
| CA | 2459091 A1 | 8/2005 |
| WO | WO-0014490 A1 | 3/2000 |

(Continued)

OTHER PUBLICATIONS

International Search Report and Written Opinion for Application No. PCT/US2014/018528, mailed on May 16, 2014, 13 pages.

*Primary Examiner* — Scott Medway

(74) *Attorney, Agent, or Firm* — Abott Medical Optics Inc.

(57) ABSTRACT

A phacoemulsification flow rate detection system and method for directly measuring the rate of fluid flowing into and out of the eye during a cataract operation.

20 Claims, 2 Drawing Sheets

(56) References Cited

U.S. PATENT DOCUMENTS

| | | | | |
|---|---|---|---|---|
| 4,851,666 | A | * | 7/1989 | Anderson et al. ........ 250/231.13 |
| 4,887,469 | A | * | 12/1989 | Shoptaw ..................... 73/861.77 |
| 5,388,466 | A | * | 2/1995 | Teunissen .................. 73/861.33 |
| 5,546,815 | A | * | 8/1996 | Wittry ........................ 73/861.77 |
| 5,557,099 | A | * | 9/1996 | Zielinski et al. ......... 250/227.11 |
| 5,638,174 | A | * | 6/1997 | Henderson ................... 356/343 |
| 5,668,327 | A | * | 9/1997 | Amemori et al. ......... 73/861.77 |
| 5,902,938 | A | * | 5/1999 | Beaudoin et al. ......... 73/861.77 |
| 6,050,656 | A | | 4/2000 | Farahi et al. |
| 6,599,277 | B2 | * | 7/2003 | Neubert ........................ 604/317 |
| 8,350,231 | B2 | | 1/2013 | Muraki |
| 2010/0130929 | A1 | * | 5/2010 | Hertweck .................... 604/118 |
| 2011/0247431 | A1 | * | 10/2011 | Moldenhauer ............ 73/861.58 |

FOREIGN PATENT DOCUMENTS

| | | |
|---|---|---|
| WO | WO-03047653 A1 | 6/2003 |
| WO | WO-2005022170 A1 | 3/2005 |
| WO | WO-2009076717 A1 | 6/2009 |

\* cited by examiner

PHACOEMULSIFICATION FLOW RATE DETECTION SYSTEM AND METHOD

FIELD OF THE INVENTION

The instant disclosure relates to the measurement of the rate of fluid flowing into and out of the eye during ophthalmic procedures that involve fluid inflow and outflow, such as during emulsification and aspiration of a cataract (outflow) and irrigation (inflow) in an operation to remove the cataract.

BACKGROUND

The crystalline lens of the eye is one of the structures that are essential to vision. In a healthy eye, the lens is a transparent, biconvex structure that refracts light to form an image on the retina. The lens also functions to change the focal distance of the eye by changing shape, so that it can focus on objects at various distances, thereby forming a sharp image of an object on the retina. This process is called accommodation.

Unfortunately, the lens is often subject to age-related damage. For example, a cataract is an often age-related clouding of the lens inside the eye that leads to a decrease in vision. It is the most common cause of blindness and is conventionally treated with surgery. Visual loss from a cataract occurs because opacification of the lens obstructs light from passing and being focused on to the retina at the back of the eye. Although a cataract is most commonly due to aging, for example, that degrades the lens proteins over time, there are many other causes as well.

More specifically, a cataract is formed of a yellow-brown pigment that is deposited within the lens and which, together with disruption of the structure of the lens fibers, leads to reduced transmission of light, which in turn leads to visual problems. Those with cataracts commonly experience difficulty discerning colors, changes in contrast, driving, reading, recognizing faces, and may have problems with glare from bright lights.

Cataracts can be addressed using surgical procedures. Almost all cataract patients' vision can be improved by surgery, with well over 90% of surgical patients achieving a corrected vision of 20/40 or better. Most commonly, cataract surgery is performed using a procedure called phacoemulsification, which uses a hand-held probe or handpiece coupled to a console. In general, no part of the probe or the console comes into contact with any part of a patient's tissues, fluids, or the like, except for the needle of the handpiece. Typically, all elements of a phacoemulsification system that come into physical contact with the patient's tissues are discarded and replaced before the system is used for another operation. The replacement parts, as well as other supplies used during the operation, are typically provided in a so-called phaco pack.

Cataract surgery involves breaking up and/or liquefying the natural lens in a process called emulsification, aspirating the emulsified lens, and irrigating the eye during the procedure. However, although important to surgical outcome, the aspiration flow rate and irrigation flow rate during surgery is not presently directly measured during surgery because of the invasive nature of flow rate detection methods, which can cause unwanted complications.

Thus, a need exists to directly measure the aspiration and irrigation flow rates during phacoemulsification surgery while mitigating the adverse effects that attend the prior art.

SUMMARY

It is to be understood that both the foregoing general description and the following detailed description are exemplary and explanatory and are intended to provide further explanation of the invention as claimed.

The present invention provides a phacoemulsification flow rate detecting system comprising at least one flow meter in communication with at least one tube/channel/fluid path through which a fluid flows during a cataract operation. The present invention may further include a sensor that may be operative to measure the rate at which the flow meter spins, and a processor to calculate the rate of the fluid flow based at least in part on the flow meter measurement. Further, a timer may be included to allow for the periodic calculation of fluid volume over a respective period based on the average fluid velocity during that period and based on the cross sectional area of the tube.

BRIEF DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION

Figure 1:
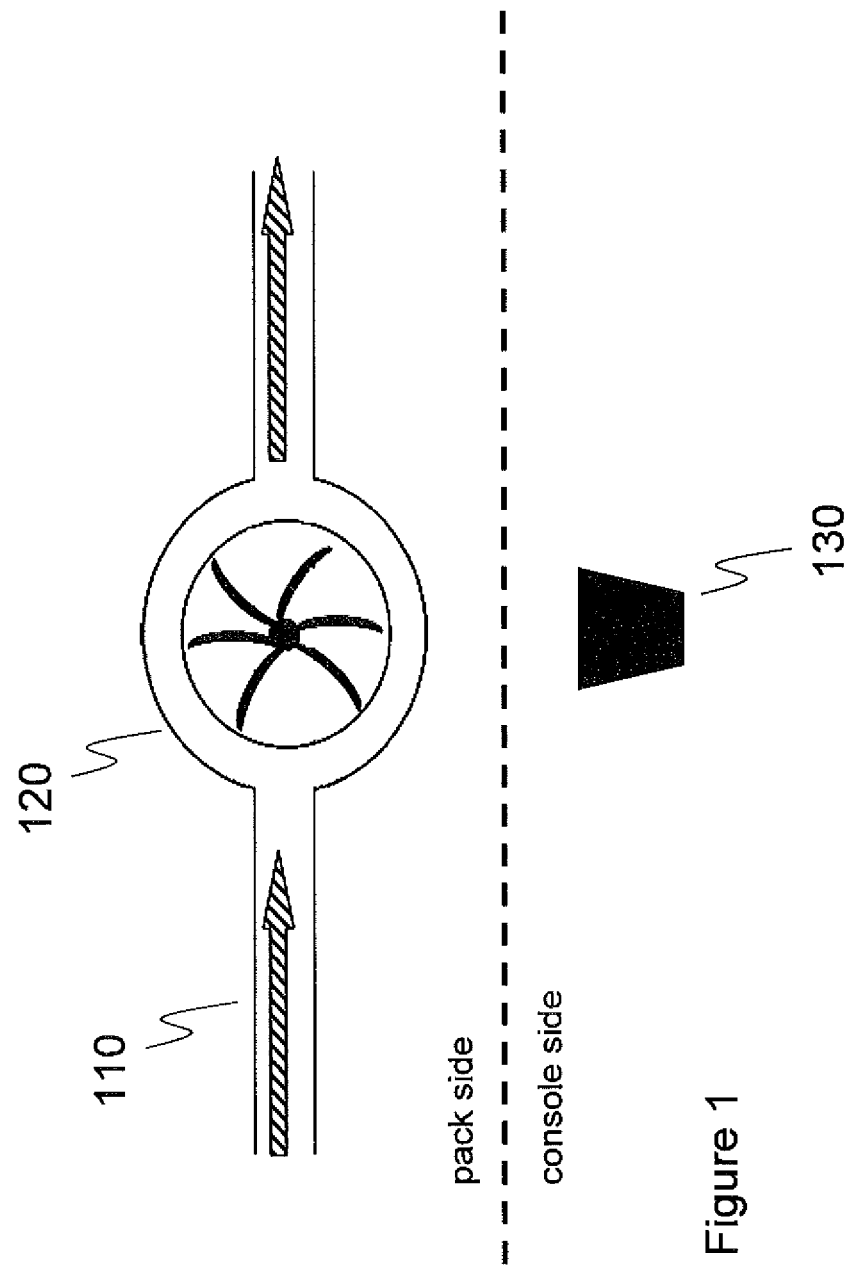
FIG. 1 illustrates a turbine flow meter embodiment of the present invention.

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical optical and surgical devices, systems, and methods. Those of ordinary skill may recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

Cataract removal by phacoemulsification can be performed at any stage in the progress of cataract development, and does not require the mature ripening of the cataract effect on the lens. Surgery is usually performed on an outpatient basis, and using local anesthesia.

Phacoemulsification typically comprises numerous steps. Typically, the subject eye is anesthetized with either a subtenon injection around the eye, or using simple eye drops. Thereafter, two cuts may be made through the clear cornea to allow insertion of instruments into the eye. Then a needle or small pair of forceps may be used to create a circular hole in the capsular bag in which the lens sits. A handheld probe or handpiece may then be used to perform the phacoemulsification, i.e., to break up and emulsify the lens into liquid using the energy of ultrasound waves. The resulting 'emulsion' may then be aspirated, i.e., sucked away. The fluid that is removed is continually replaced with an irrigating salt solution to prevent collapse of the structure of the anterior chamber of the eye. Then, a lens, most commonly a foldable intraocular lens (IOL), is inserted to the capsular bag as a replacement for the natural lens that was removed. Finally, balanced salt solution may be injected into the corneal wounds to cause the area to swell and seal the incision.

In current systems for performing such a procedure there is no direct measurement of the aspiration and irrigation flow rates. Instead, aspiration is quantified by vacuum pressure, and irrigation is quantified by irrigant pressure such as may be indicated, for example, by bottle height. Neither of these quantifications uses a direct measurement of flow rate, and consequently, it may be difficult and imprecise to correlate these quantifications to flow rate. Such correlation may be important to moderate the intraocular pressure during the procedure, and to monitor for the presence of occlusions in the fluid being aspirated, for example.

In an exemplary embodiment of the herein disclosed apparatus and methods, an element is provided in the aspiration and irrigation apparatus that is caused to rotate by the flow of fluid. In embodiments, the rotating element may include a turbine or paddle wheel. As the fluid flows, it turns the rotating element. A sensor element, such as an optical sensor, may detect the passing of the turbine or paddle fins past a stationary point. From this, a spin rate may be determined, and flow rate may be calculated from the spin rate and the known cross-section of the tube through which the fluid is flowing.

Most commonly, the phacoemulsification procedure may be performed using a handpiece coupled to a console, in combination with disposable materials that may be disposed of after being used to perform the phacoemulsification procedure. The disposable materials may be provided in a so-called phaco pack. In an embodiment, the rotating elements may be included as a feature of tubing provided in the phaco packs. In such an arrangement, the optical sensor may be included in the console, either alone or in cooperation with other elements of the console. This combination of elements may provide for an unobtrusive method of directly measuring fluid flow, and may allow for measurement of either or both of the aspiration and the irrigation flows.

As illustrated in FIG. 1, a miniature inline meter 120, such as a miniature turbine flow meter 120, may be used with an optical sensor assembly 130 in at least one tube 110 to measure flow rate. The tube 110 and flow meter 120 may be resident in a cassette or phaco pack, for example, with the optical sensor assembly 130 being resident in a larger console. The flow meter 120 may be responsive to very low flow rates, such as flow rates in a range of about 0 cc/min to about 200 cc/min.

Commonly used inline flow meters are not responsive to very low flow rate due, in part, to the direct methods employed to read a rate of spin of the flow meter. The bearings for the inline turbine 120 may be within the housing of the turbine 120, which may allow for a nearly "frictionless" spinning of the turbine 120. Said another way, the impact on the flow within tube 110 is minimized as there is no direct physical measurement of the spin rate of the turbine 120 which is allowed to freely spin about an axle. In an embodiment of the present invention, the turbine 120 has only one moving part, namely the turbine wheel assembly, which may include, for example, a plurality of blades affixed to a center spine which may freely rotate about the axle.

The optical sensor assembly 130 may produce at least one beam of light from a light source, such as a laser, for example, which may be partially reflected back to the optical sensor assembly 130 for measurement. The reflection of the projected light may be from a reflective material (not shown) located on the opposite side of the turbine 120 from the optical sensor assembly 130, or located on the blades of the turbine 120. The light source may also be reflected by particles in the fluid being measured, such particles being deliberately added to the solution to aid in measurement or included as a necessary aspect of the measured fluid.

In an embodiment of the present invention, a light from the optical sensor assembly 130 is passed through turbine 120 substantially parallel to the axle of turbine 120 and is reflected back through the turbine 120 from a reflective surface thereon, or on the blades thereof, to an optical reader within the optical sensor assembly 130. The optical reader may take the form of a photo transistor and may read the returning light as a pulse train that may be converted into a volumetric flow value.

In another embodiment of the present invention, a light from the optical sensor assembly 130 is projected onto turbine 120 substantially perpendicular to the axle of turbine 120 and is reflected back to optical sensor assembly 130 by reflective material on the turbine 120, or on the blades of the turbine 120. As may be appreciated by the discussion above, the optical reader may read the returning light as a pulse train, wherein each pulse may be representative of a passing blade.

Although variations in the type and intensity of the light projected by optical sensor assembly 130 may be calibrated to allow for passing through certain liquid types, the present invention may most often be utilized with balanced salt solutions (BSS) and thus may allow for the use of coherent or incoherent light sources. Similarly, the speed of flow to be measured may not be that high. For example, typical irrigation flow rates during phacoemulsification surgery may range between 0 cc/min to about 100 cc/min and may average, for example, about 45 cc/min.

In an embodiment of the present invention, a phaco pack having at least one turbine in at least one line may be inserted into a surgical console for use in a surgery. The turbine may be aligned with a portion of the console having at least one optical sensor assembly so as to enable the measuring of the spin rate of the turbine blades. Although accurate alignment of the turbine to the optical sensor assembly is preferred, the optical sensor assembly may provide a wide area of both light emission and receiving capabilities to allow for movement of the phaco pack and/or the line during use. In this way, the installation of the phaco pack need only be substantially in the targeted position, and may allow room for movement and/or disruption of the turbine location. Additionally, the use of only active components in the console side may help reduce the cost of phaco packs and may allow for easier maintenance and/or calibration of the optical sensor assembly.

In an embodiment of the present invention, some portion of the flow meter may be metallic and may be detectable by a magnetic sensor. For example, all or a portion of the blades of the turbine 120 may be composed entirely or comprise a detectable amount of metal. By way of further example, a blade may have an amount of metal disposed near the bottom of the blade which may allow a magnetic sensor to detect when individual blades are passing by or are in the closest proximity. Additionally, blades and/or flow meter assemblies containing metals may further be coated with a plastic or Teflon, for example, to prevent corrosion and/or reaction with the fluid being measured.

Figure 2:
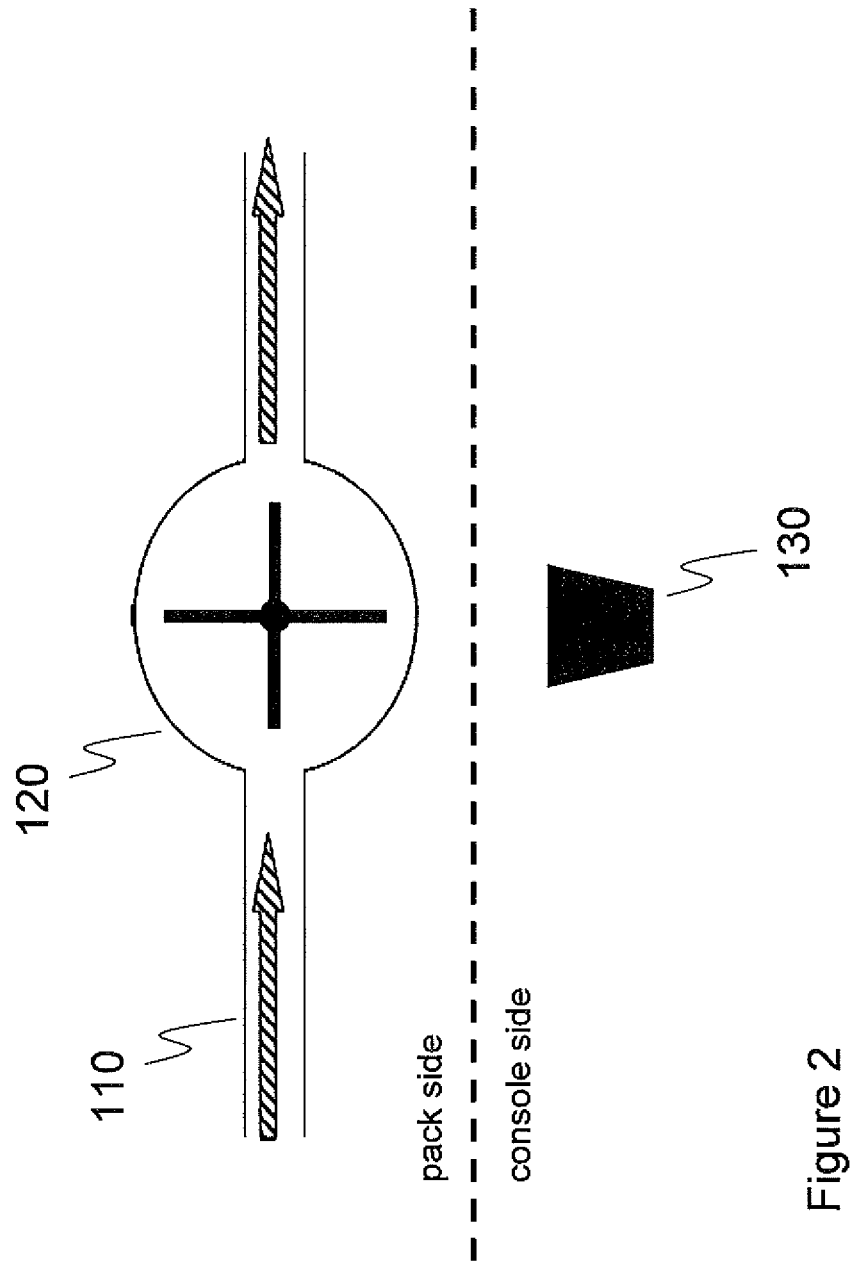
FIG. 2 illustrates a paddle wheel flow meter embodiment of the present invention.

FIG. 2 illustrates a paddle type flow meter suitable for use with the present invention. Although such a flow meter may be measured in a similar manner as the turbine type flow meter discussed above, the paddle type flow meter may provide some advantages. For example, the more linear design of the paddle blades may provide a larger surface area for optical measurement based on the reflection of light from the blades. Similarly, measurement along the axle's axis for the paddle wheel may prove to be more optically distinctive and may thus allow for more accurate measurements at higher velocities. Furthermore, such a paddle blade design may allow for greater ease of flow (especially when only four blades are used) and may allow for more viscous or particle laden fluids to more easily pass by the flow meter without substantially altering the spin of the flow meter or slowing/jamming the flow meter altogether.

As described herein, a tube (and in particular tube 110) includes not only commonly used tubing, but any device, fluid path, or system which may be employed to convey a fluid. By way of non-limiting example only, a tube may include molded channels and/or a combination of molded channels and common tubing/piping.

Although the disclosure has described and illustrated exemplary embodiments with a certain degree of particularity, it is noted that the description and illustrations have been made by way of example only. Numerous changes in the details of construction, combination, and arrangement of parts and steps may be made. Accordingly, such changes are intended to be included within the scope of the disclosure, the protected scope of which is defined by the claims.

What is claimed is:

1. A phacoemulsification flow rate detection system, comprising:
  a cassette, comprising:
    at least one channel through which a fluid flows during phacoemulsification;
    at least one flow meter in fluid communication with the at least one channel, wherein the flow meter includes a rotating element having a plurality of blades arranged to come into contact with the flowing fluid, wherein each blade of the plurality of blades has a linear design; and
  a console, comprising:
    an optical sensor comprising at least one light source and at least one optical reader, wherein the at least one light source is operative to produce at least one beam of light to be passed through the flow meter substantially parallel to an axle of the flow meter, and wherein the at least one optical reader is operative to measure a spin rate of the flow meter via at least a portion of the at least one beam of light reflected back from a reflective material through the flow meter to the at least one optical reader of the optical sensor, wherein the reflective material is located on a surface that opposes the optical sensor and is on the opposite side of the flow meter from the optical sensor; and
    a processor in data communication with the optical sensor and operative to calculate the flow rate of the fluid flow based at least in part on the spin rate measured from the flow meter.

2. The system of claim 1, further comprising a timer coupled to the processor;
  wherein the at least one light source and the at least one optical reader of the optical sensor are operative to measure a velocity of the fluid through a predetermined cross sectional area of the channel; and
  wherein the processor is operative to periodically calculate a volume of the fluid during at least one respective period based on an average of the fluid velocity during the period and based on the cross sectional area, and to calculate therefrom the flow rate of the fluid.

3. The system of claim 2, wherein the optical sensor measures an instantaneous velocity of the fluid, and the average velocity is determined by averaging the instantaneous velocity at a beginning of the period and at an end of the period.

4. The system of claim 3, wherein a duration of the period is between 1 ms and 100 ms.

5. The system of claim 1, wherein the optical sensor and the processor are communicatively coupled to the flow meter.

6. The system of claim 1, wherein the optical sensor is arranged in the console to prevent contact with the fluid.

7. The system of claim 1, wherein the rotating element is coupled to a lumen of the channel and the plurality of blades are impelled by the flowing fluid causing the rotating element to rotate;
  wherein the optical sensor is operative to measure the flow meter by counting a number of times during a period that a one of the plurality of blades passes a predetermined point.

8. The system of claim 1, wherein the fluid passing through the channel is one of an emulsion being aspirated from an eye, and an irrigant being provided to the eye.

9. The system of claim 8, further comprising at least one each of an aspirating channel and an irrigating channel, wherein the processor is operative to correlate the aspirant and the irrigant to determine a net inflow or outflow of fluid into or out of the eye, respectively.

10. The system of claim 9, wherein the processor is operative to calculate an intraocular pressure based on the correlation.

11. The system of claim 1, wherein the flow meter is at least partially metallic.

12. A method of detecting a fluid flow rate during an eye operation, comprising:
  aspirating a fluid from an eye through a fluid path in a cassette during the eye operation;
  measuring a spin rate of a flow meter arranged in the fluid path in the cassette with an optical sensor arranged in a console via at least one beam of light produced by at least one light source of the optical sensor, wherein the at least one beam of light is passed through the flow meter substantially parallel to an axle of the flow meter, and wherein at least a portion of the at least one beam of light is reflected back from a reflective material through the flow meter to at least one optical reader of the optical sensor, wherein the reflective material is located on a surface that opposes the optical sensor and is on the opposite side of the flow meter from the optical sensor and the flow meter includes a rotating element having a plurality of blades arranged to come into contact with the aspirated fluid, wherein each blade of the plurality of blades has a linear design; and
  calculating, with a processor in data communication with the optical sensor, the fluid flow rate based at least in part on the spin rate of the flow meter.

13. The method of claim 12, wherein the measuring is based on at least one of a measurement of a velocity of the fluid, a pressure of the fluid, and a temperature of the fluid.

14. The method of claim 12, further comprising:
periodically calculating a volume of the fluid flowing past a predetermined point through the fluid path during at least one respective period based on an average fluid velocity during that period and a cross sectional area of the fluid path; and
calculating therefrom the flow rate of the fluid.

15. The method of claim 12, wherein the optical sensor is arranged to prevent contact with the fluid.

16. The method of claim 12, wherein the optical sensor measures the flow rate of the fluid by counting a number of times during a period that a blade of the plurality of blades of the rotating element passes a predetermined point.

17. The method of claim 12, further comprising administering an irrigation fluid through a second fluid path and correlating an amount of aspirant removed from the eye and an amount of irrigant provided to the eye to determine a net inflow or outflow of fluid into or out of the eye, respectively.

18. The method of claim 12, further comprising calculating an intraocular pressure based on the correlation.

19. The system of claim 1, wherein the at least one optical reader is configured to read the at least a portion of the at least one beam of light reflected back from a reflective material through the flow meter as a pulse train.

20. The method of claim 12, wherein the at least one optical reader reads the at least a portion of the at least one beam of light reflected back from a reflective material through the flow meter as a pulse train.

* * * * *